United States Patent
Withers et al.

(10) Patent No.: US 6,284,494 B1
(45) Date of Patent: *Sep. 4, 2001

(54) METHODS AND COMPOSITIONS FOR SYNTHESIS OF OLIGOSACCHARIDES USING MUTANT GLYCOSIDASE ENZYMES

(75) Inventors: Stephen G. Withers; Lloyd MacKenzie, both of Vancouver; Qingping Wang, Kirkland, all of (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/091,272

(22) PCT Filed: Dec. 12, 1996

(86) PCT No.: PCT/CA96/00841

§ 371 Date: Sep. 29, 1998

§ 102(e) Date: Sep. 29, 1998

(87) PCT Pub. No.: WO97/21822

PCT Pub. Date: Jun. 19, 1997

Related U.S. Application Data (63) Continuation-in-part of application No. 08/571,175, filed on Dec. 12, 1995, now Pat. No. 5,716,812.

(51) Int. Cl.$^7$ ............ C12P 19/44; C12P 19/12; C12N 9/24; C12N 9/26; C12N 9/42
(52) U.S. Cl. ............ 435/74; 435/100; 435/200; 435/201; 435/209
(58) Field of Search ............ 435/74, 100, 200, 435/201, 209, 440

(56) References Cited

U.S. PATENT DOCUMENTS

| | | | |
|---|---|---|---|
| 4,918,009 | 4/1990 | Nilsson | 435/73 |
| 5,246,840 | 9/1993 | Nilsson | 435/101 |
| 5,372,937 | 12/1994 | Nilsson | 435/74 |

FOREIGN PATENT DOCUMENTS

| | | |
|---|---|---|
| 0226563 | 6/1987 | (EP) . |
| 87/05936 | 10/1987 | (WO) . |
| 89/09275 | 10/1989 | (WO) . |
| 94/29477 | 12/1994 | (WO) . |
| 95/18232 | 7/1995 | (WO) . |
| 95/18864 | 7/1995 | (WO) . |

OTHER PUBLICATIONS

Withers et al., "Mechanistic Comsequences of Mutation of the Active Site Nucleophile GLU 358 in Agrobacterium β–Glucosidase" *Biochemistry* 31: 9979–9985 (1992).

Trimbur et al., A β–Glucosidase from an Agrobacterium sp.: Structure and Biochemistry in *ACS Sympsium* Series (1992) pp. 42–55.

Gebler et al., "Substrate–Induced Inactivation of a Crippled β–Glucosidase Mutant: Identification of the labeled Amino Acid and Mutagenic Analysis of Its Role", *Biochemistry* 34: 14547–14553 (1995).

Wang et al., "Identification of the Acid/Base catalyst in *Agrobacterium faecalis* β–glucosidase by kinetic analysis of mutants" *Biochemistry* 34: 14454–14562 (1995).

Wang et al., "Substrate–assisted Catalysis in Glycosidases" *J. Amer. Chem. Soc.* 117: 10137–1–138 (1995).

Witt et al., "6–Phospho–β–galactosidases of Gram Positive and 6–phospho–β–glucosidase B of Gram–Negative bacteria: comparison of structure and function by kinetic and immunological methods and mutageneisis of the lacG gene of *Staphyloccous aureus*" *Protein Engineering* 6: 913–920 (1993).

Nikolova et al., "Transglycosylation by Wild Type and Mutants of a β–1,4–Glycosidase from *Cellulomonas fimi* (Cex) for synthesis of Oligosaccharides", *Annals NY Acad. Sci.* 799: 19–25 (1996).

Wang, et al. (1994) "Changing Enxymic Reaction Mechanisms by Mutagenesis: Conversion of a Retaining Glucosidase to an Inverting Enzyme", J. Am. Chem. Soc. 116:11594–11595.

Svensson, (1988) FEBS Letters 230:72–76.

Nagashima, et al. (1992) Biosci. Biotech. Biochem. 56:207–210.

*Primary Examiner*—Elizabeth Slobodyansky
(74) *Attorney, Agent, or Firm*—Oppedahl & Larson LLP (57) ABSTRACT

Mutant glycosidase enzymes are formed in which the normal nucleophilic amino acid within the active site has been changed to a non-nucleophilic amino acid. These enzymes cannot hydrolyze disaccharide products, but which can still form them. Using this enzyme, oligosaccharides are synthesized by preparing a mixture of an α-glycosyl fluoride and a glycoside acceptor molecule; enzymatically coupling the α-glycosyl fluoride to the glycoside acceptor molecule to form a glycosyl glycoside product using the mutant glycosidase enzyme; and recovering the glycosyl glycoside product. Particular enzymes include a mutant form of Agrobacterium β-Glucosidase in which the normal glutamic acid residue at position 358 is replaced with an alanine residue.

2 Claims, 2 Drawing Sheets

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 24
      (B) TYPE: nucleic acid
      (C) STRANDEDNESS: single
      (D) TOPOLOGY: linear    (ii) MOLECULE TYPE: other DNA

```
    (iii) HYPOTHETICAL: no (iv) ANTI-SENSE: no (v) FRAGMENT TYPE: internal (ix) FEATURE:
          (A) NAME/KEY:
          (B) LOCATION:
          (C) IDENTIFICATION METHOD:
          (D) OTHER INFORMATION: primer for site directed mutagenesis to
              produce E358A mutant of Agrobacterium beta-glucosidase (xi) SEQUENCE DESCRIPTION: SEQ ID NO:1:

TACATCACCG CAAACGGCGC CTGC                                          24
```

METHODS AND COMPOSITIONS FOR SYNTHESIS OF OLIGOSACCHARIDES USING MUTANT GLYCOSIDASE ENZYMES

This application is a U.S. National Phase, filed under 35 USC § 371, of PCT/CA96/00841, which is a continuation-in-part of U.S. patent application Ser. No. 08/571,175 filed Dec. 12, 1995, now U.S. Pat. No. 5,716,812.

BACKGROUND OF THE INVENTION

This application relates to methods and compositions for synthesizing oligosaccharides, and to the oligosaccaharide products which can be obtained using such methods and compositions.

Oligosaccharide are copounds with considerable potential both as therapeutics and as reagents for clinical assays. The very nature of the saccharide subunits, however, makes the sythensis of oligosaccharide of potential interest a daunting task because of many posibilities for information of positional isomers in which different substituent groups on the sugars become involved in bond formation and potential for the fomation of different anomeric forms. Because of these factors, chemical synthezis of most oligosaccharides while possible is not generally feasible on a commercial scale because of poor yields of the desired product.

An alternative to chemical synthesis of oligosacaharides is enzymatic synthesis. In particular, enzymatic synthesis using glycosyl transferases, glycosidases or combinations thereof has been considered as a possible approach to the synthesis of oligosaccharides.

Glycosyl transferases catalyse the reaction

Glycosyl transferases can be very effective for producing specific products with good stereochemical and regiochemical control, if a transferase with the desired specificity is available. The enzymes can be expensive and hard to handle since they are often membrane-associated and unstable, however, and the required nucleotide sugar substrates can be quite expensive. Furthermore, glycosyl transferases possessing the desired specificity to make many interesting oligosaccharides are not available.

Glycosidases catalyze the reaction and synthesize oligosaccharides when the reaction is run in reverse from the normal direction. In addition, oligosaccharide synthesis can be achieved by adding a second sugar to the reaction mixture which competes with water and reacts in its place with the first sugar in a transglycosylation reaction. Glycosidases are generally available and easy to handle and have the potential to make many different products using inexpensive substrates. Unfortunately, it is difficult to control the reverse hydrolysis reaction which leads to poor product yields. In addition, while the stereochemical control (i.e., the formation of only one anomer) is generally good, it is hard to predict or control the regiochemistry (i.e., the formation of 1–2 vs 1–3 vs 1–4 vs 1–6 bonds).

To realize the potential of enzymatic oligosaccharide synthesis, there is therefore a need for a synthetic approach which avoids the drawbacks of the known techniques. It is an object of this invention to provide such a technique which permits the synthesis of a wide variety of oligosaccharides in good yield, and to provide enzymes suitable for practicing these techniques.

SUMMARY OF THE INVENTION

These and other objects of the invention can be achieved through the use of mutant glycosidase enzymes, which cannot hydrolyze disaccharide products, but can still form them. Thus, a first aspect of the present invention is a method for forming an oligosaccharide. In this method a mixture of a glycosyl donor and a glycoside acceptor molecule is prepared. The glycosyl donor is selected from among molecules having substituents at the 1-position which are good leaving groups. The glycosyl donor is then enzymatically coupled to the glycoside acceptor molecule to form a glycosyl glycoside product using a mutant glycosidase enzyme in which one of two key amino acids has been changed, and the glycosyl glycoside product is recovered. In the case of a "retaining" glycosidase, the mutant enzyme is one in which the normal nucleophilic amino acid within the active site had been changed to a non-nucleophilic amino acid. In the case of an "inverting" glycosidase, the mutant enzyme in one in which the amino acid which normally functions as a base has been replaced by a non-ionizable amino acid. In both cases, the glycosyl donor is selected to have the opposite anomeric configuration from the desired product.

A further aspect of the present invention is a mutant glycosidase enzyme of the retaining type, in which the normal nucleophilic amino acid within the active site has been changed to an amino acid other than glutamic acid or aspartic acid. One such enzyme is a mutant form of Agrobacterium β-Glucosidase in which the normal glutamic acid residue at position 358 is replaced with an alanine residue.

A further aspect of the present invention is a mutant glycosidase enzyme of the inverting type, in which the normal amino acid that functions as a base within the active site has been changed to a non-ionizable amino acid.

DETAILED DESCRIPTION OF THE INVENTION

This invention relates to mutant forms of glycosidase enzymes. Glycosidase enzymes can be classified as being either "retainers" because they retain the stereochemistry of the bond being broken during hydrolysis, or "inverters" because they invert the stereochemistry of the bond being broken during hydrolysis.

Figure 1:
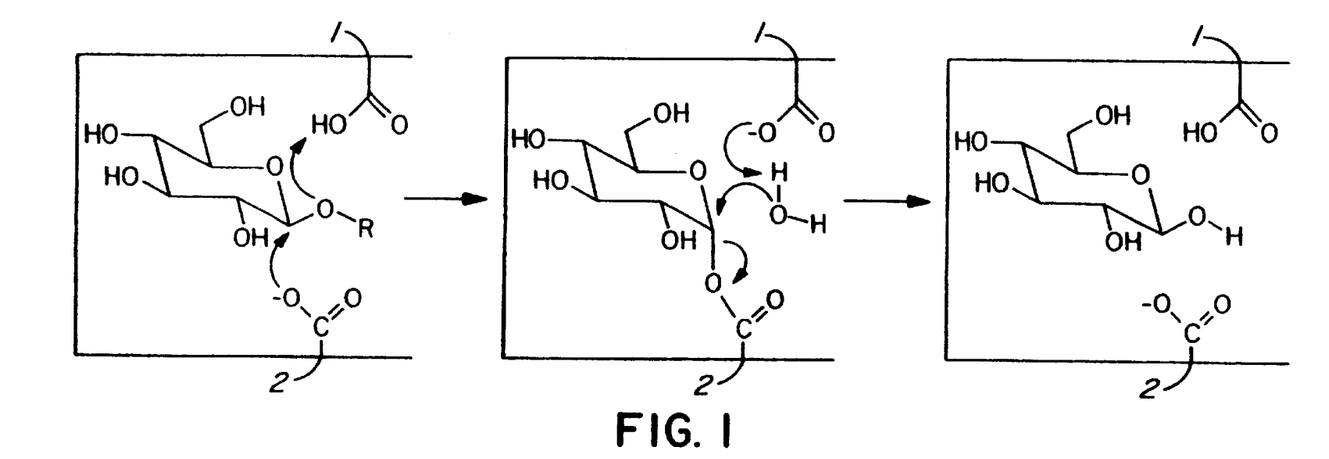
FIG. 1 shows the hydrolysis of a disaccharide within the active site of a normal glycosidase enzyme which retains stereochemical configuration during hydrolysis.

Normal stereochemistry retaining enzymes have two carboxylic acid groups in the active site of the enzyme as shown generally in FIG. 1. One of these groups functions as an acid/base catalyst (labeled as group 1 in FIG. 1) and the other as a nucleophile (group 2 in FIG. 1). The nucleophile group 2 forms a glycosyl-enzyme intermediate which is then cleaved by the acid/base catalyst group 1 to result in a hydrolyzed glycoside in which the stereochemistry has been maintained.

Figure 2:
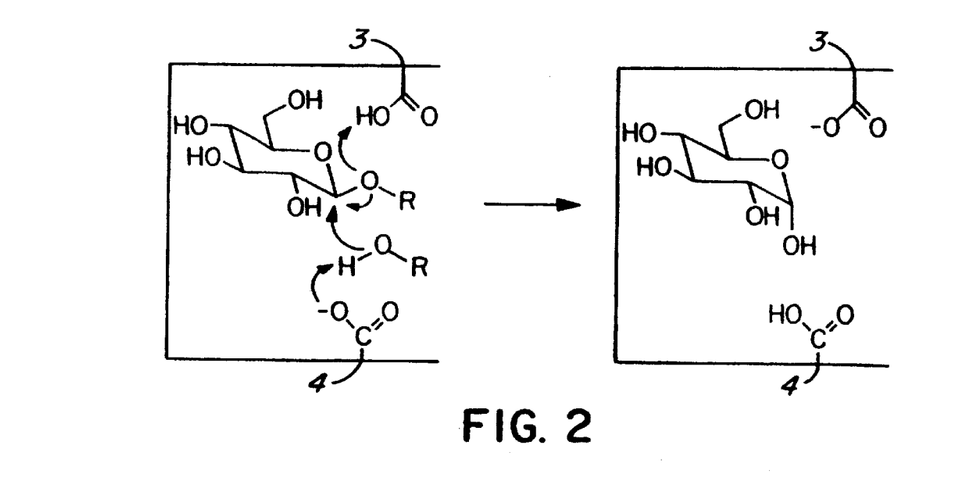
FIG. 2 shows the hydrolysis of a disaccharide within the active site of a normal glycosidase enzyime which inverts stereochemical configuration during hydrolysis.

Normal stereochemistry inverting enzymes also have two carboxylic acid groups in the active site of the enzyme as shown generally in FIG. 2. In inverting enzymes, however, one of these groups functions as an acid catalyst (labeled as group 3 in FIG. 2) and the other as a base catalyst (group 4 in FIG. 2). The acid catalyst group 3 protonates the hemiacetal-hydroxyl group of the glycosyl donor molecule, making it a good leaving group, at the same time that the base catalyst group 4 deprotonates a donor molecule (water or HOR) allowing it to replace the leaving hydroxyl group with inversion of stereochemistry.

The present invention provides mutant forms of both retaining and inverting enzymes in which one of the two carboxylic acid amino acids in the active site has been replaced with a different amino acid. Such mutations provide enzymes which do not catalyze the hydrolysis of oligosaccharides, but which nevertheless retain activity to synthesize oligosaccharides with good control over the stereochemistry and regiochemistry of reaction.

Enzymes to which the methodology of the present invention may be employed include, for example, β-Glucosidases, β-galactosidases, β-mannosidases, β-acetyl glucosaminidases, β-N-acetyl galactosaminidases, β-xylosidases, β-fucosidases, cellulases, xylanases, galactanases, mannanases, hemicellulases, amylases, glucoamylases, α-glucosidases, α-galactosidases, α-mannosidases, α-N-acetyl glucosaminidases, α-N-acetyl galactos-aminidases, α-xylosidases, α-fucosidases, neuraminidases/sialidases such as those from: Agrobacterium sp., Bacillus sp., Caldocellsm sp., Clostridium sp., *Escherichia coli*, Kluveromyces sp., Klebsiella sp., Lactobacillus sp., Aspergillus sp., Staphylococcus sp., Lactobacillus sp., Butyrovibrio sp., Ruminococcus sp., Sulfolobus sp., Schizophyllum sp., Trichoderma sp., Cellulomonas sp., Erzwinia sp., Humicola sp., Pseudomonas sp., Thermoascus sp., Phaseolus sp., Persea sp., Fibrobacter sp., Phanaerochaete sp., Microbispora sp., Saccharomyces sp., *Hordeum vulgare*, Glycine max, Saccharomycopsis sp., Rhizopus sp., Nicotiana, Phaseolus sp., rat, mouse, rabbit, cow, pig, and human sources. Preferred enzymes in accordance with the Invention are mutant forms of retaining glycosidase enzymes.

Figure 3:
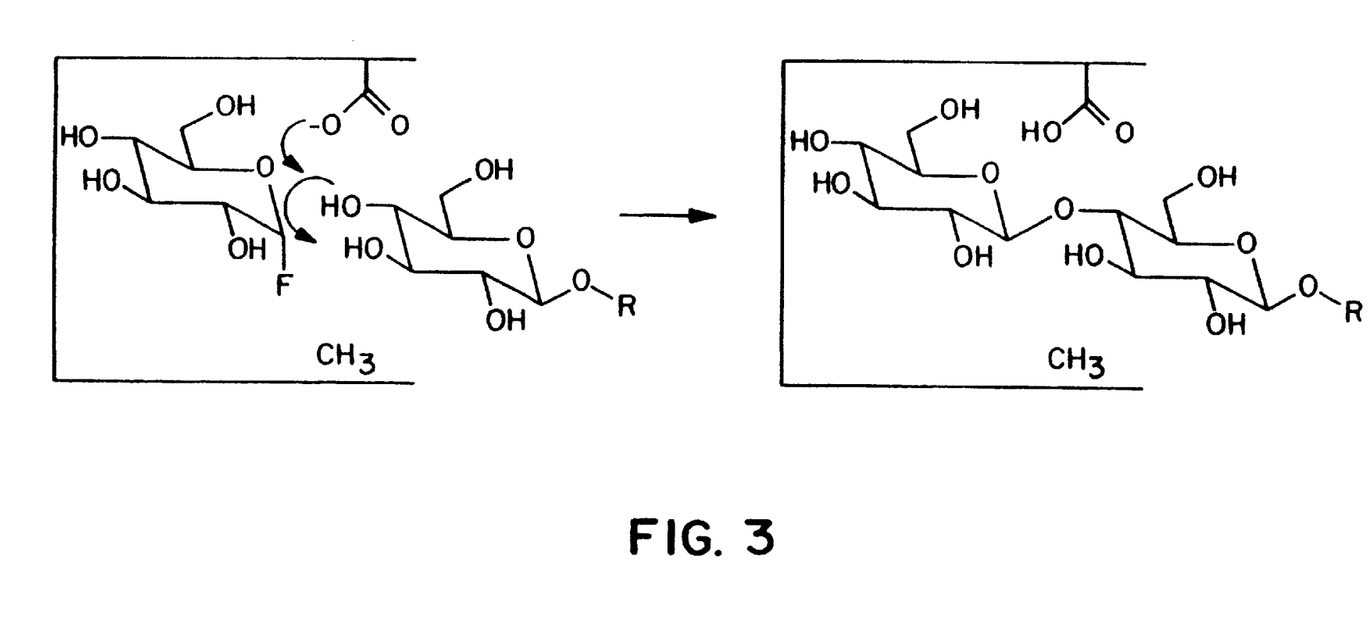
FIG. 3 shows the synthesis of a disaccharide within the active site of a mutant glycosidase within the scope of the present invention.

In the enzymes of the present invention, one of the two amino acid residues with the active carboxylic acid side chains is changed to a different amino acid which does not act as a nucleophile (in the case of a retaining enzyme) or as a base catalyst (in the case of an inverting enzyme). Thus, in general, the substitution will involve replacing the glutamic acid or aspartic acid residue of the wild-type enzyme with alanine, glycine, valine, leucine, isoleucine, serine, threonine, cysteine, methionine, asparagine, glutamine, histidine, proline, phenylalnine, or tyrosine. Preferably, the substituted amino acid will have a side chain of approximately equal or smaller size to the side chain of the wild-type amino acid residue to avoid significant changes to the size and shape of the active site. Enzymes mutated in this way are inactive with the normal substrates, and thus cannot hydrolyze oligosaccharide products. They can, however, catalyze the coupling of modified glycosyl donor molecules to modified acceptors, for example the coupling of an α-glycosyl fluoride donor to a β-glycoside acceptor as shown in FIG. 3. This reaction proceeds with substantial yield because the reverse hydrolysis reaction does not occur, and with good stereochemical and regiochemical control.

The site for mutation in a retaining glycosidase may be identified after trapping of the glycosyl-enzyme intermediate in the active site using one of the following approaches. First, the intermediate may be trapped by rapid denaturation of the enzyme, or a mutant thereof, after incubation in the presence of a substrate. Alternatively, the intermediate may be trapped using a modified substrate which forms a relatively stable glycosyl-enzyme intermediate. Possible modified substrates which could be used include 2-deoxy-2-halo glycosyl derivatives, 2-deoxy-2,2-dihalo glycosyl derivatives, 5-halo glycosyl derivatives, cyclitol epoxides, epoxyalkyl glycosides, glycosyl methyl triazenes and other glycosyl derivatives bearing a reactive functional group at their anomeric center.

Once this intermediate has been trapped, the labeled enzyme is then cleaved into peptides by use of a protease or by specific chemical degradation, and the peptide bearing the sugar label then located in a chromatogram or other separation method and its aminoacid sequence determined. Comparison of this sequence with that of the intact enzyme readily identifies the amino acid of interest.

Identification of the labeled peptide may be achieved by a number of methods. These could include use of a radiolabeled glycosyl derivative, then searching for the radiolabeled peptide(s); comparative peptide mapping by HPLC or by LC/MS; LC/MS—MS analysis of the peptides, monitoring in neutral loss mode for the loss of the sugar in the collision cell.

The catalytic nucleophile may also be identified in the three-dimensional structure of the enzyme determined by X-ray crystallography or NMR spectroscopy by inspection of the active site region, searching for a Glu or Asp residue. This would be facilitated by the inclusion of a substrate or an analogue in the active site of the enzyme.

Alternatively, the catalytic nucleophile may be identified by the generation of mutants in which each Clu and Asp residue which is shown to be highly conserved within a homologous (or analogous) family of enzymes has been replaced, individually, by Ala. Identification of the mutant which is capable of utilizing the "wrong" glycosyl fluoride as a substrate will thereby allow identification of the residue of interest.

The site for mutation in an inverting glycosidase may be identified by inspection of the three dimensional structure, where available, or by mutation of each glutamic acid and aspartic acid residue which is conserved within a sequence-related family to alanine and assaying each mutant for its ability to synthesize oligosaccharides using the corresponding glycosyl fluoride (i.e, a β-glycosyl fluoride for an α-glycosidase mutant or an α-glycosyl fluoride for a β-glycosidase mutant).

Using these procedures, we have determined the appropriate site for mutation for several glucosidase enzymes. Thus, in Agrobacterium β-glucosidase, the mutant enzyme of the invention is prepared by replacing the glutamic acid at position 358 with another amino acid, for example alanine. Mutant α-amylase (human or porcine) in accordance with the invention has the aspartic acid at position 197 replaced with another amino acid, for example alanine, while in yeast α-glucosidase the aspartic acid at position 216 is replaced.

Once the site for mutation has been identified, a mutant gene is prepared using site directed mutagenesis to arrive at the desired result. In general, this involves the construction of a plasmid containing the coding sequence for the wild-type gene, and isolation of single stranded DNA. Copies are then made of the isolated plasmid DNA using a template dependant DNA polymerase and a primer which overlaps the site of the desired mutation and which differs from the wild-type sequence in the manner necessary to yield the desired mutation. The mutated plasmid is then transformed into a host organism, e.g., E. coli. Transformants are initially selected using a marker contained within the plasmid, and then further selected by sequencing of the expressed glycosidase enzyme to confirm the nature of the mutation.

Mutant enzymes according to the invention may be purified from the growth medium of the host organism by column chromatography, for example on DEAE-cellulose if desired. High levels of purity are not required for use in catalyzing oligosaccharide synthesis, however, provided that impurities with wild-type glycosidase activity must be substantially absent.

The enzymes of the invention are used to couple α-modified glycosyl donors with glycoside acceptor. Preferred donor molecules are glycosyl fluorides, although other groups which are reasonably small and which function as relatively good leaving groups can also be used. Examples of other glycosyl donor molecules include glycosyl chlorides, acetates, propionates, and pivaloates, and glycosyl molecules modified with substituted phenols. The donor molecules may be monosaccharides, or may themselves contain multiple sugar moieties.

Glycosyl fluorides can be prepared from the free sugar by first acetylating the sugar and then treating it with HF/pyridine. This will generate the thermodynamically most stable anomer of the protected (acetylated) glycosyl fluoride. If the less stable anomer is desired, it may be prepared by converting the peracetylated sugar with HBr/HOAc or with HCL to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g., NaOMe/MeOH). In addition, glycosyl donor molecules, including many glycosyl fluorides can be purchased commercially. Thus a wide range of donor molecules are available for use in the methods of the present invention.

The glycoside acceptor used in the method of the present invention may be essentially any glycoside molecule containing from 1 to 10 sugar moieties. The acceptor molecule may be substituted at positions away from the group which is coupled by the enzyme. Thus, the glycoside acceptor may be a monosaccharide, an oligosaccharide, or a sugar-containing molecule such as an aminoglycoside antibiotic.

When the donor molecule is an α-glycosyl donor molecule, the glycoside acceptor used is a β-glycoside acceptor, and vice versa. The acceptor and donor are combined in an aqueous buffer (for example 250 mM sodium phosphate buffer, pH 7.0 or 250 mM ammonium carbonate buffer, pH 7.75) in a mole ratio (acceptor/donor) of about 1 to 2.5, more preferably 1.1 to 2.0 together with a catalytic amount (i.e., about 0.02 to 0.5 mg/ml) of mutant enzyme and incubated at around 25° C. for a period of time sufficient to produce significant yields of product, for example 12 hours to 4 days.

To remove the buffer from the product when phosphate buffer is used, the reaction mixture is combined with 5 volumes of methanol, filtered through a silica plug (5 cm) and concentrated in vacuc. For carbonate buffer, the mixture is co-evaporated with water (3 times) in vacuo. The residues from either procedure are then dissolved in acetonitrile/methanol, filtered and purified by silica gel chromatography or HPLC. The purified product can then be dissolved in water and freeze-dried or crystallized to yield a solid product.

On a commercial scale, it may be advantageous to immobilize the enzyme to facilitate its removal from a batch of product and subsequent reuse. Such immobilization could be accomplished by use of a fusion protein in which the mutant glycoside is engineered onto another protein with high affinity for an insoluble matrix. For example, a fusion protein with a cellulose binding protein prepared in the manner described by Ong et al., "Enzyme Immobilization Using the Cellulose-Binding Domain of a Cellulomonas fimi Exoglucanase", *Biotechnology* 7: 604–607 (1989) could be used in accordance with the invention.

The method of the invention can be used to make a wide variety of oligosaccharides. Particularly useful oligosaccharides which can be made by this method include cello-oligosaccharides and cello-oligosaccharide glycans which are very difficult to synthesize chemically but which are of interest because of their use in the study of cellulases, and oligosaccharide-based inactivators of cellulases which can be used to study cellulase activity and which have potential as antifungal agents, particularly in the control of wood-degrading fungi. Another application of the present invention is the synthesis of malto-oligosaccharide derivatives with a β-linked sugar (glucose, galactose, mannose, fructose, N-acetylglucosamine) attached at the non-reducing end. Such products would be useful in clinical assays for α-amylase.

EXAMPLE 1

*Escherichia coli* strains JM101 (Viera & Messing, 1988) and RZ1032 (Kunkel et al., 1987) have been described. Plasmid pTZ18Rabg was constructed by taking the coding sequence of the β-glucosidase gene (abg) from pABG5 (Wakarchuk et al., 1986) and inserting it into pTZ18R. JM101 was maintained on M9 minimal media. Plasmid containing strains were grown in Luria broth containing 100 ug/mL ampillicin.

Single-stranded DNA was isolated by the following method. Cultures were grown on TYP (16 g/L tryptone, 16 g/L yeast extract, 5 g/L NaCl, 2.5 g/L K2HPO4) medium containing 100ug/mL armpicillin and 109 PFU/mL helper phage M13K07 (viera and Messing, 1988). Kanamycin (50 ug/mL) was added 1 h after inoculation, and the culture was grown 6–10 h at 37° C. Phagemid were precipitated with 1.7 M ammonia acetate and 12% (w/v) PEG-6000. Single-stranded DNA was isolated from the phagemid by method of Kristensen et al (Kristensen et al., 1987). Uracil-containing template was generated by growing the plasmid in strain RZ1032. Site-directed mutants were generated by the method of Kunkel (Kunkel, 1987) with modifications for phagemid vectors. The specific mutation of the active site nucleophile (E358) were carried out with the oligonucleotide primer: TACATCACCG CAAACGGCGC CTGC SEQ ID NO.: 1

T7 DNA polymerase was used for the extension reactions. After in vitro mutagenesis, the plasmid DNA (pTUG10NAbgE358A) was transformed into JM101. Transformants were selected on LB agar containing 2% 5-bromo-4-chloro-3-indolyl-β-D-glucopyranoside, lmM isopropyl-β-D-thiogalactopyranoside and 100 ug/mL ampillicin. Possible mutants were screened by single,track sequencing and confirmed by complete sequencing reactions. The entire coding region of Agrobacterium β-glucosidase was then sequenced to confirm that only the desired mutations was present. DNA sequencing was performed by the method of Tabor and Richardson (Tabor & Richardson (1987), *Proc. Natl. Acad. Sci. U.S.A.* 84, 4767). Expression level of the mutant protein was monitored by SDS-PAGE followed by Western blot analysis with wild type enzyme as a control. Kristensen, T., Voss, H., & Ansorge, W. (1987) *Nucleic Acids Res.* 15, 5507. Kunkel, T. A., Roberts, J. D., & Zakour, R. A. (1987) *Methods Enzymol.* 154, 367. Tabor, S. & Richardson, C. C. (1987). Viera, J. & Messing, J. (1988)*Gene* 19, 259. Wakarchuk, W. W., Kilburn, D. G., Miller, R. C., Jr., & Warren, R. A. J. (1986) *Mol. Gen. Genet.* 205, 146.

Agrobacterium E358A-β-Glucosidase was purified by modification of the method employed for isolation of the native enzyme from *E. coli*. Kempton & Withers, (1992) *Biochemistry*, 31, 9961, except that enzyme presence and activity was measured with 2,4-dinitrophenyl-β-D-glucoside with sodium azide (Wang et al., (1994) *J. Amer. Chem. Soc.*, 116, 11594.

Protein was expressed in *E. coli* JM11 from the lac promotor of pTZ18R. Cells grown overnight in 200 mL of Typ Amp media at 30° C. were used to inoculate the fermentor (15–20 L) at a level of 0.5–1.0%. The cells were grown to 2–3 $O_{600}$, treated with 0.1 mM IPTC and harvested when growth reached 6–7 $O_{600}$.

Cells were harvested by Sharples continuous centrifugation at 31,000×g and the cell paste stored at −20° C. The cell pellet from the 15 L culture was thawed at 25° C. and resuspended in 1–2 mL of 50 mM sodium phosphate, 2 mM EDTA buffer, pH 7.0, per gram of cell paste. The mixture was then passed twice through a French pressure cell and cell debris removed by centrifugation (20,000×g for 30 min.). Steptomycin sulphate was added to this extract to a concentration of 1.5% (w/v). The mixture was stirred for 4 hr. at 4° C. and then centrifuged (20,000×g for 30 min.) to remove the precipitated nucleic acids. The extract was then loaded onto a DEAE-Sephacel column (45 cm×5 cm) equilibrated with 50 mM sodium phosphate 2 mM EDTA buffer, pH 7.0. The column was eluted with 2×1 L linear gradient of 0–1 M sodium chloride in starting buffer. Fractions containing the highest activity of E358A β-glucosidase were pooled, dialyzed overnight against 50 mM sodium phosphate buffer, pH 7.0 and concentrated using Amicon Centiprep 30 centrifuge ultrafiltration devices.

Silver stained SDS-PAGE showed the single column purification of E358A β-glucosidase to be approximately 95% homogenous. Protein concentration was determined using the absorbance value of $E_{280,0.1\%}$=2.184 cm−1. The mass of the E358A mutant was confirmed to be 58 amu's lower than that of the wild-type enzyme by electrospray mass spectrometry. Protein was used without any further purification for transglycosylation experiments.

EXAMPLE 2

α-Galactosyl fluoride (0.35 mmoles) and p-nitrophenyl-β-D-glucoside (0.22 mmoles) were dissolved in 3.0 ml of 250 mM ammonium carbonate buffer (pH 7.75). 25 ul of an 8.75 mg/ml stock solution of E358A β-glucosidase was added. After incubation at 25° C. for 48 hours, TLC analysis (Merck Kieselgel 60 F-254 plates, solvent system 7:2:1 ethyl acetate, methanol, water) indicated the reaction had gone to completion. Buffer was removed from the reaction system by transferring to a round bottom flask and co-evaporating with water (3×25 ml) in vacuo. The residue was dissolved in acetonitrile/methanol (10:1), filtered and purified by silica gel chromatography. The resulting oil was dissolved in water and freeze dried to yield 85 grams (84% yield) of an amorphous solid.

The amorphous solid was analyzed by $^1$H NMR, Mass Spectroscopy and elemental analysis. The product was identified as p-nitrophenyl-4-O-(glucopyranosyl)-β-D-galactopyranoside.

EXAMPLE 3

α-Glucosyl fluoride was coupled to a variety of aryl-glucoside acceptors using E-358A β-glucosidase. Reactions were run at a donor to acceptor mole ratio of 1.1–1.3 in ammonium carbonate buffer (pH 7.7) for a period of 48 hours. The products were recovered and purified by silica gel chromatography or HPLC, and analyzed by KH NMR and Mss Spectroscopy. The results are summarized in Table 1. As can be seen, the two main products in all cases were the β-1,4 linked cellobioside and cellotrioside, both of which were formed in substantial yields. These products all have potential utility as cellulase inhibitors and substrates.

This example was repeated by using additional aryl-glycoside acceptors at a donor to an acceptor mole ratio of 1.1–2.1 and the results are summarized in Table 1(a).

TABLE 1

Transglycosylation Reactions of Agrobacterium β-Glucosidase E358A Mutant with α-Glucosyl Fluoride (Donor) and Aryl-Glucosides (Acceptors).

| | | PRODUCTS (% YIELD) | | | |
| | | β-1,4 linked | | | |
| # | ACCEPTOR | Cellobioside | Cellotrioside | Cellotetraoside | Total Yield† |
| 1 |  | 48% | 34% | — | 82% |

TABLE 1-continued

Transglycosylation Reactions of Agrobacterium β-Glucosidase E358A Mutant with α-Glucosyl Fluoride (Donor) and Aryl-Glucosides (Acceptors).

| # | ACCEPTOR | PRODUCTS (% YIELD) β-1,4 linked | | | Total Yield† |
|---|---|---|---|---|---|
| | | Cellobioside | Cellotrioside | Cellotetraoside | |
| 2 | 4-nitrophenyl β-D-glucoside | 38% | 24% | 10% | 72% |
| 3 | 2-nitrophenyl β-D-glucoside | 41% | 29% | 6% | 76% |
| 4 | 2,4-dinitrophenyl β-D-glucoside | 34% | 29% | 7% | 70% |
| 5 | 2-(methoxycarbonyl)phenyl β-D-glucoside | 44% | 24% | — | 68% |
| 6 | 4-(methoxycarbonyl)phenyl β-D-glucoside | 37% | 36% | — | 73% |
| 7 | 2-(carbamoyl)phenyl β-D-glucoside | 54% | 22% | — | 76% |

TABLE 1-continued

Transglycosylation Reactions of Agrobacterium β-Glucosidase E358A Mutant with α-Glucosyl Fluoride (Donor) and Aryl-Glucosides (Acceptors).

| # | ACCEPTOR | PRODUCTS (% YIELD) β-1,4 linked | | | Total Yield† |
|---|---|---|---|---|---|
| | | Cellobioside | Cellotrioside | Cellotetraoside | |
| 8 | (2-nitro-4-carbomethoxyphenyl β-D-glucoside) | 22% | 46% | — | 68% |
| 9 | (2-carbomethoxy-4-nitrophenyl β-D-glucoside) | 26% | 34% | 6% | 66% |
| 10 | (2-carboxamido-4-nitrophenyl β-D-glucoside) | 42% | 34% | 3% | 79% |
| 11 | (2-deoxy-2-fluoro 2,4-dinitrophenyl β-D-glucoside) | 38% | 42% | 4% | 84% |
| 12 | (2-deoxy-2-chloro 2,4-dinitrophenyl β-D-glucoside) | 42% | 40% | 4% | 86% |
| 13 | (phenyl 1-thio-β-D-glucoside) | 34% | 22% | — | 56% |
| 14 | (benzyl β-D-glucoside) | 22% | 37% | — | 59% |

TABLE 1-continued

Transglycosylation Reactions of Agrobacterium β-Glucosidase E358A Mutant with α-Glucosyl Fluoride (Donor) and Aryl-Glucosides (Acceptors).

| # | ACCEPTOR | PRODUCTS (% YIELD) β-1,4 linked | | | Total Yield† |
|---|---|---|---|---|---|
| | | Cellobioside | Cellotrioside | Cellotetraoside | |
| 15 |  | 12% | 24% | — | 36% |

†Yields are based on isolated products.
Reactions were set up with 1.1–1.3 equivalents of α-glucosyl fluoride relative to the acceptor.
Typical reaction performed on 25–50 mg of acceptor and larger scale reactions from 100 mg–1000 mg.

TABLE 1(a)

Additional Examples of Transglycosylation Reactions of Agrobacterium β-Glucosidase E358A Mutant with α-Glucosyl Fluoride (Donor) and Aryl-Glycosides (Acceptors).

| # | ACCEPTOR | PRODUCTS (% YIELD) β-1,4 linked | | | Total Yield† |
|---|---|---|---|---|---|
| | | Cellobioside | Cellotrioside | Cellotetraoside | |
| 1 |  | — | 84% | 6% | 90% |
| 2 |  | 28% | 50% | — | 78% |
| 3 |  | 50% | 16% | — | 66% |
| 4 |  | 37% | 34% | — | 71% |

TABLE 1(a)-continued

Additional Examples of Transglycosylation Reactions of Agrobacterium β-Glucosidase E358A Mutant with α-Glucosyl Fluoride (Donor) and Aryl-Glycosides (Acceptors).

| # | ACCEPTOR | PRODUCTS (% YIELD) β-1,4 linked | | | Total Yield† |
|---|---|---|---|---|---|
| | | Cellobioside | Cellotrioside | Cellotetraoside | |
| 5 | [4-(difluoromethyl)phenyl β-D-glucopyranoside structure] | 48% | 21% | — | 69% |

†Yields are based on isolated products.
Reactions were set up with 1.1–2.1 equivalents of α-glucosyl fluoride relative to the acceptor.
Typical reaction performed on 5–50 mg of acceptor and larger scale reactions from 100 mg–1000 mg.

EXAMPLE 4

To evaluate the effect of the donor molecule on the products formed, the experiment of Example 3 was repeated using different aryl-glycosides as donors. The results of this experiment are shown in Table 2. As can be seen, selection of the nature of the donor moiety in some cases shifts the reaction to the production of β-1,3 linkages, but in each case still produced a good yield of product.

TABLE 2

Transglycosylation Reactions of Agrobacterium β-Glucosidase E358A Mutant with α-Glucosyl Fluoride (Donor) and Aryl-Glycosides (Acceptors).

| # | ACCEPTOR | PRODUCTS (% YIELD) β-1,4 linked (or if *β-1,3 linked to acceptor) | | | Total Yield† |
|---|---|---|---|---|---|
| | | Disaccharide | Trisaccharide | Tetrasaccharide | |
| 1 | [4-nitrophenyl xylopyranoside structure] | 12%* | 51%* | 3% | 66% |
| 2 | [2-nitrophenyl xylopyranoside structure] | 14%* | 44%* | 4% | 62% |
| 3 | [4-nitrophenyl galactopyranoside structure] | 6#  | 8%# | — | 14% |
| 4 | [4-nitrophenyl mannopyranoside structure] | 18%# | 36%# | — | 54% |

TABLE 2-continued

Transglycosylation Reactions of Agrobacterium β-Glucosidase E358A Mutant with α-Glucosyl Fluoride (Donor) and Aryl-Glycosides (Acceptors).

| | | PRODUCTS (% YIELD) β-1,4 linked (or if *β-1,3 linked to acceptor) | | | |
|---|---|---|---|---|---|
| # | ACCEPTOR | Disaccharide | Trisaccharide | Tetrasaccharide | Total Yield† |
| 5 |  | 31% | 42% | 6% | 79% |

†Yields are based on isolated products.
Product linkage type not yet determined.
Reactions were set up with 1.1–1.3 equivalents of α-glucosyl fluoride relative to the acceptor.
Typical reaction performed on 25–50 mg of acceptor and larger scale reactions from 100 mg–1000 mg.

EXAMPLE 5

Transglycosylation reactions according to the invention were performed to couple α-galactosyl fluoride with various aryl-glycosides. Reactions were run at a donor to acceptor mole ratio of 1.5–2.0 in amonium carbonate buffer (pH 7.7) for a period of 48 hours. The products were recovered and purified by silica gel chromatography or HPLC, and analyzed by $^1$H NMR and mass spectroscopy. The results are summarized in Table 3. In each case, a good yield of a disaccharide product was obtained. In each case for which the product linkage has been determined, the linkage type was β-1,4.

This example was repeated using additional aryl-glycoside acceptors with a donor acceptor mole ratio of 1.5–2.0 with 5–50 or 100–1,000 mg of acceptor. The results are shown in Table 3(a).

TABLE 3

Transglycosylation Reactions of Agrobacterium β-Glucosidase E358A Mutant with α-Galactosyl Fluoride (Donor) and Aryl-Glycosides (Acceptors).

| | | PRODUCTS (% YIELD) β-1,4 linked(unless otherwise stated) | |
|---|---|---|---|
| # | ACCEPTOR | Disaccharide | Total Yield† |
| 1 |  | 84% | 84% |
| 2 |  | 81%# | 81% |
| 3 |  | 54% | 54% |

TABLE 3-continued

Transglycosylation Reactions of Agrobacterium β-Glucosidase E358A Mutant with α-Galactosyl Fluoride (Donor) and Aryl-Glycosides (Acceptors).

| | | PRODUCTS (% YIELD) β-1,4 linked(unless otherwise stated) | |
| --- | --- | --- | --- |
| # | ACCEPTOR | Disaccharide | Total Yield† |
| 4 | [structure: 2-chloro-4-nitro-2-nitrophenyl glycoside] | 64% | 64% |
| 5 | [structure: p-nitrophenyl mannoside] | 66%# | 66% |

†Yields are based on isolated products.
Product linkage type not yet determined.
Reactions were set up with 1.5–2.0 equivalents of α-galactosyl fluoride relative to the acceptor.
Typical reaction performed on 25–50 mg of acceptor and larger scale reactions from 100 mg–1000 mg.
Note: Galactose as a donor acts as a chain terminator under these conditions, so only disaccharides are produced.

TABLE 3(a)

Additional Examples of Transglycosylation Reactions of Agrobacterium β-Glucosidase E358A Mutant with α-Galactosyl Fluoride (Donor) and Aryl-Glycosides (Acceptors).

| | | PRODUCTS (% YIELD) β-1,4 linked | |
| --- | --- | --- | --- |
| # | ACCEPTOR | Disaccharide | Total Yield† |
| 1 | [structure: 4-methylumbelliferyl glycoside] | 79% | 79% |
| 2 | [structure: 2,4-dinitrophenyl glycoside] | 68% | 68% |

TABLE 3(a)-continued

Additional Examples of Transglycosylation Reactions of Agrobacterium β-Glucosidase E358A Mutant with α-Galactosyl Fluoride (Donor) and Aryl-Glycosides (Acceptors).

| | | PRODUCTS (% YIELD) β-1,4 linked | |
|---|---|---|---|
| # | ACCEPTOR | Disaccharide | Total Yield† |
| 3 |  | 75% | 75% |
| 4 |  | 72% | 72% |

†Yields are based on isolated products.
Reactions were set up with 1.5–2.0 equivalents of α-galactosyl fluoride relative to the acceptor.
Typical reaction performed on 25–50 mg of acceptor and larger scale reactions from 100 mg–1000 mg.
Note: Galactose as a donor acts as a chain terminator under these conditions, so only disaccharides are produced.

EXAMPLE 6

Transglycosylation reactions according to the invention were performed to couple α-glucosyl fluoride with various cellobiosyl derivatives. Reactions were run at a donor to acceptor mole ratio of 1.1–1.4 in phosphate buffer (pH 7.0) for a period of 24 hours. The products were recovered and purified by silica gel chromatography or HPLC, and analyzed by $^1$H NMR and mass spectroscopy. The results are summarized in Table 4. In each case, good yield of β-1,4-linked trisaccharide and tetrasaccharide products were obtained.

TABLE 4

Transglycosylation Reactions of Agrobacterium β-Glucosidase E358A Mutant with α-Glucosyl Fluoride (Donor) and Cellobiosyl Derivatives (Acceptors).

| | | PRODUCTS (% YIELD) β-1,4 linked | | |
|---|---|---|---|---|
| # | ACCEPTOR | Trisaccharide | Tetrasaccharide | Total Yield† |
| 1 |  | 79% | 13% | 92% |
| 2 |  | 64% | 21% | 85% |

TABLE 4-continued

Transglycosylation Reactions of Agrobacterium β-Glucosidase E358A Mutant with α-Glucosyl Fluoride (Donor) and Cellobiosyl Derivatives (Acceptors).

| # | ACCEPTOR | PRODUCTS (% YIELD) β-1,4 linked | | Total Yield† |
|---|---|---|---|---|
| | | Trisaccharide | Tetrasaccharide | |
| 3 | [structure] | 71% | 15% | 86% |
| 4 | [structure] | 31% | 28% | 59% |
| 5 | [structure] | 22% | 21% | 43% |

†Yields based on isolated products. Reactions were set up with 1.1–1.4 equivalents of α-glucosyl fluoride relative to the acceptor.
Typical reaction performed on 25–50 mg of acceptor and larger scale reactions from 100 mg–1000 mg.

EXAMPLE 7

A transglycosylation reaction according to the invention was performed to couple α-galactosyl fluoride with p-nitrophenyl-α-D-maltoside. Reactions were run at a donor to acceptor mole ratio of 1.1–1.4 in ammonium carbonate buffer (pH 7.7) for a period of 48 hours. The products were recovered and purified by HPLC, and analyzed by $^1$H NMR and mass spectroscopy. p-Nitrophenyl-4'-O-[β-D-galactopyranosyl]-α-D-maltoside was recovered in 64% yield.

EXAMPLE 8

Identification of the nucleophile of Agrobacterium faecalis β-glucosidase was performed by trapping the intermediate formed between the enzyme and 2',4'-dinitrophenyl 2-deoxy-2-fluoro-β-D-glucoside (2F-DNPG).

Synthesis of 2',4'-dinitrophenyl 2-deoxy-2-fluoro-β-D-glucoside has been reported previously (Withers, S. G., Warren, R. A. J., Street, I. P., Rupitz, K., Kempton, J. B. & Aebersold, R. (1990) *J. Amer. Chem. Soc.* 112, 5887–5889). Briefly this involved treatment of 1,3,4,6-tetra-O-acetyl 2-deoxy-2-fluoro-D-glucose (Adam. M. (1982) *J. Chem. Soc. Chem. Commun.* 730–731) with 1.1 equivs of hydrazine acetate in dimethyl formamide and heating for 3 minutes. This was then cooled to room temperature, and reaction monitored until complete as determined by TLC. The resultant hemiacetal was then dissolved in dimethyl formamide (1 g in 10 mL) containing 4A molecular sieves and DABCO (0.15 g) and 1-fluoro-2,4-dinitrobenzene added. The reaction mixture was stirred at room temperature for 1.5 hours, then the sieves were removed by filtration and the solvent evaporated in vacuo to yield an oil which was dissolved in chloroform and washed successively with a saturated solution of sodium bicarbonate, then water, and dried over MgSO4. The solvent was evaporated in vacuo to give an oil which solidified on trituration with ethanol. The product was then recrystallized from ethanol to yield the per-O-acetylated glycoside. This product was deprotected by suspending a sample of the glycoside (70 mg) in dry methanol (15 mL) and adding acetyl chloride (1 mL). This reaction mixture was stirred for 24 h at 4 °C., then solvent removed by evaporation in vacuo, and the product crystallized from ethanol.

A sample of β-glucosidase (400 μg, 7.8 mg/mL) was inactivated with 2F-DNPG (0.32 mM) in 50 mM sodium phosphate buffer, pH 6.8 at 37° C. by incubation for 5 minutes. The labeled enzyme was then completely digested using 1:100 pepsin (w/w; enzyme:substrate) in 50 mM sodium phosphate buffer, pH 2.0,at room temperature. The proteolytic digest (10 μg) was loaded onto a C18 column (Reliasil, 1×150 mm), then eluted with a gradient of 0–60% solvent B over 20 minutes followed by 100% B for 2 minutes at a flow rate of 50 μl/minute.

The intact enzyme, unlabeled and labeled with 2F-DNPC, and the eluted materials from the C18 column were evaluated by mass spectrometry. Mass spectra were recorded on a PE-Sciex API III triple quadrupole mass spectrometer (Sciex, Thornhill, Ont., Canada) equipped with an ionspray ion source. Protein or peptide samples were separated by reverse phase HPLC on an Ultrafast Microprotein Analyzer (Michrom BioResources Inc., Pleasanton, Calif.) directly interfaced with the mass spectrometer, using solvent A: 0.05% trifluoroacetic acid, 2% acetonitrile in water and solvent B: 0.045% trifluoroacetic acid, 80% acetonitrile in water. A post-column flow splitter was used to introduce 15% of the HPLC eluate into the mass spectrometer, while 85% was collected for further analysis.

Intact protein samples (10 μg, native or labeled) were introduced into the mass spectrometer through a microbore PLRP column (1×50 mm) on the Michrom HPLC system (solvent system: 20–100% solvent B over 10 minutes, 100% solvent B over 2 minutes). The quadrupole mass analyzer (in the single quadrupole mode) was scanned over a m/z range 300–2400 Da with a step size of 0.5 Da and a dwell time of 1 ms per step. The ion source voltage (ISV) was set at 5 kV and the orifice energy (OR) was 80 V. Protein molecular weights were determined from this data using the deconvolution software supplied by Sciex.

The single quadrupole mode (normal LC/MS) MS conditions used were identical to those for analysis of the intact protein. The neutral loss MS/MS spectra were obtained in the triple quadrupole neutral loss scan mode searching for the mass loss corresponding to the loss of the label from a peptide ion in the singly or doubly charged state. Thus, scan range: m/z 300–1200; step size: 0.5 Da; dwell time: 1 ms per step; ISV: 5 kV; OR: 80; RE1=115; DM1=0.16; R1=0 V; R2=−50 V; RE3=115; DM3=0.16; Collision gas thickness (CGT): 3.2–3.6×10$^{14}$ molecules/cm$^2$. (CGT=320–360). To maximize the sensitivity of neutral loss detection, normally the resolution is compromised without generating artifact neutral loss peaks.

Peptic proteolysis of 2FGlu-labeled Abg resulted in a mixture of peptides which was separated by reverse phase-HPLC, using the ESIMS as a detector. When the spectrometer was scanned in the normal LC-MS mode, the total ion chromatogram (TIC) of the 2FGlu-Abg digest displayed a large number of peaks, reflecting the complexity of the mixture. The 2FGlu-labeled peptide was then identified in a second run using the tandem mass spectrometer set up in the neutral loss scanning mode (MS/MS). In this mode, the ions are subjected to limited fragmentation by collisions with argon in a collision cell. The ester linkage between the 2FGlu label and the peptide is one of the more labile linkages present, readily susceptible to homolytic cleavage. Indeed, the collision conditions employed were sufficient to break the ester bond but not generally the peptide bonds. This results in the loss of a neutral 2FGlumoiety, leaving the peptide moiety with its original charge. The two quadrupoles are then scanned in a linked manner such that only ions differing in m/z by the mass corresponding to the label can pass through both quadrupoles and be detected. In some cases, however, it may be necessary to scan for m/z differences of one half or one third the mass of the neutral species as the peptide may be doubly or triply charged.

When the spectrometer was scanned in the neutral loss MS/MS mode, searching for a mass loss corresponding to the 2FGlu moiety of m/z 165, two peaks were observed in the total ion chromatogram which are not seen in an equivalent chromatogram of a peptic hydrolysate of unlabeled Abg, suggesting that this was the peptide of interest.

The identity of this peptide can be easily probed by calculation of its mass. The labeled peptide observed of m/z 871 corresponds to an unlabeled peptide 706 Da while that at m/z1035 corresponds to a peptide of mass 870 Da. A search of the amino acid sequence of Abg for all possible peptides of mass 730 Da and 870 Da containing the same Glu or Asp residue produced a short list of candidates from which the true sequence was determined by MS/MS analysis.

EXAMPLE 9

A fusion protein combining the E358A mutant of Agrobacterium β-glucosidase and the cellulose-binding domain of *Cellulomonas fimi* was prepared using the general approach of Ong et al., supra. Plasmid pTUG10NAbgE358A (encoding AbgE358A) and plasmid pEO1 (encoding Abg-CBDcex) were each cut with Avr II and Sph I. The 0.78 kb fragment liberated from pTUG10NAbgE358A carrying the mutation was isolated by GeneClean as was the 4.2 Kb fragment from pEO1. The two fragments were ligated together (T4 DNA ligase) effectively replacing the corresponding wild-type fragment in pEO1 with the mutation. The ligation mixture was transformed to electrocompetent *E. coli* DH5αF'. Ampicillin resistant clones were selected and the plasmid DNA isolated by the Quiagen method. This yielded pAMC (encoding AbgE358A-CBDcex). The mutation was confirmed by sequencing and mass spectroscopy.

The plasmid was transformed to electrocompetent *E. coli* TB-1 for expression of the recombinant protein. To prepare the fusion protein, the host organism is grown under inducing conditions. Cells are harvested by centrifugation, washed and broken in a French press. PMSF and pepstatin are immediately added to inhibit proteolysis after which cellular debris is removed by centrifugation. Fusion protein is then purified by cellulose affinity chromatography on Whatman CF1 cellulose, followed by elution and concentrated by ultrafiltration. The purified fusion protein may be immobilized on a cellulose matrix for use in oligosaccharide synthesis. The presence of the mutant E358A can be confirmed by reaction with dinitrophenyl-β-D-glucoside in the presence of sodium azide and/or by SDS-PAGE.

What is claimed is:

1. A method for synthesizing an oligosaccharide comprising the steps of:
   (a) combining a glycosyl donor molecule and a glycoside acceptor molecule in a reaction mixture, said glycosyl donor molecule having a β configuration and said glycoside acceptor molecule having an α configuration, or vice versa; and
   (b) enzymatically coupling the donor molecule to the acceptor molecule using Agrobacterium β-glucosidase in which amino acid 358 has been changed from glutamic acid to an amino acid with a non-carboxylic acid side chain.

2. The method of claim 1, wherein the, amino acid 358 has been changed from glutamic acid to alanine.

* * * * *